US00RE36103E

United States Patent [19]

Winter et al.

[11] E Patent Number: Re. 36,103

[45] Reissued Date of Patent: Feb. 16, 1999

[54] PROCESS FOR THE PREPARATION OF A SYNDIOTACTIC POLYOLEFIN AND CATALYST THEREFOR

[75] Inventors: Andreas Winter; Jürgen Rohrmann; Martin Antberg; Volker Dolle; Walter Spaleck, all of Frankfurt am Main, Germany

[73] Assignee: Targor GmbH, Germany

[21] Appl. No.: 278,504

[22] Filed: Jul. 21, 1994

Related U.S. Patent Documents

Reissue of:

[64] Patent No.: 5,132,381
Issued: Jul. 21, 1992
Appl. No.: 490,833
Filed: Mar. 8, 1990

[30] Foreign Application Priority Data

Mar. 11, 1989 [DE] Germany ..... 3907694.3

[51] Int. Cl.[6] ..... C08F 4/642; C08F 10/00

[52] U.S. Cl. ..... 526/160; 502/117; 556/52; 556/53; 556/11; 526/127; 526/132; 526/351; 526/150

[58] Field of Search ..... 556/52, 53; 502/117; 526/160

[56] References Cited

U.S. PATENT DOCUMENTS 4,892,851 1/1990 Ewen et al. .

FOREIGN PATENT DOCUMENTS 0 128 045 12/1984 European Pat. Off. .
3 726 067 2/1989 Germany .

OTHER PUBLICATIONS

Lotz, B. et al., Macromolecules 21:2375–2382 (1988).
Ewen, J. A. et al., J. Am. Chem. Soc. 110:6255–6256 (1988).

*Primary Examiner*—Edward J. Smith

[57] ABSTRACT

A syndiotactic polyolefin is obtained in a high yield by polymerization or copolymerization of an olefin of the formula $R^a$—CH=CH—$R^b$ in the presence of a catalyst consisting of a metallocene of the formula I

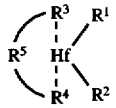

(I)

and an aluminoxane. This polyolefin has a very high syndiotactic index.

At a low polymerization temperature, a polyolefin having a low average molecular weight and narrow molecular weight distribution is obtained, and at a high polymerization temperature a polymer having a high average molecular weight and a wide molecular weight distribution is obtained.

Shaped articles produced from the polymers are distinguished by a high transparency, flexibility, tear strength and excellent surface gloss.

12 Claims, No Drawings

PROCESS FOR THE PREPARATION OF A SYNDIOTACTIC POLYOLEFIN AND CATALYST THEREFOR

Matter enclosed in heavy brackets [ ] appears in the original patent but forms no part of this reissue specification; matter printed in italics indicates the additions made by reissue.

The invention relates to a novel process which can be employed on a large industrial scale for the preparation of a syndiotactic polyolefin.

Syndiotactic polyolefins, in particular syndiotactic polypropylene, are known per se. However, it has not yet been possible to prepare such polymers in an adequate yield under polymerization conditions which are of interest industrially. Thus, it is known that syndiotactic polypropylene can be prepared by polymerization of propylene at −78° C. in the presence of a catalyst system consisting of $VCl_4$ anisole, heptane and diisobutylaluminum chloride (compare B. Lotz et al., Macromolecules 21, (1988), 2375). However, the syndiotactic index (=76.9%) and the yield (=0. 16%) are too low.

It is furthermore known that a syndiotactic polypropylene having a narrow molecular weight distribution can be obtained in a significantly improved yield with the aid of a catalyst consisting of isopropylene(cyclopentadienyl)(1-fluorenyl)zirconium dichloride or isopropylene-(cyclopentadienyl)(1-fluorenyl)hafnium dichloride and a methylaluminoxane at a temperature of 25° to 70° C. (compare J. A. Ewen et al., J. Am. Chem. Soc., 110 (1988), 6255). Nevertheless, the molecular weight of the polymer which can be achieved by means of the zirconium compound is still too low. The syndiotactic indices which can be achieved are moreover still in need of improvement.

Although the narrow molecular weight distributions are suitable for injection molding and precision injection molding, a medium to broad molecular weight distribution would be advantageous for deep drawing, extrusion, hollow body blow molding, plate casting and the production of films.

It is known that the polymerization of ethylene in the presence of two or more metallocene catalysts simultaneously can produce polyethylene having a broad molecular weight distribution (compare EP 128,045). However, because several catalyst systems are used, the polymer is of poor homogeneity. The catalysts described moreover produce only atactic polymer, which is of only minor interest industrially, on polymerization of 1-olefins.

The object was to discover a process which produces a highly syndiotactic polyolefin of very high molecular weight and broad molecular weight distribution.

It has been found that the object can be achieved by using special hafnocene catalyst.

The invention thus relates to a process for the preparation of a syndiotactic polyolefin by polymerization or copolymerization of an olefin of the formula $R^aCH{=}CHR^b$, in which $R^a$ and $R^b$ are identical or different and denote a hydrogen atom or an alkyl radical having 1 to 28 carbon atoms, or $R^a$ and $R^b$, with the atoms joining them, can form a ring, at a temperature of −60° to 200° C. under a pressure of 0.5 to 100 bar in solution, in suspension or in the gas phase in the presence of a catalyst which consists of a metallocene as the transition metal component and an aluminoxane of the formula II

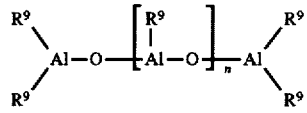

(II)

for the linear type and/or of the formula III

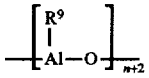

(III)

for the cyclic type, in which, in the formulae II and III, $R^9$ denotes a $C_1$–$C_6$-alkyl group or a $C_6$–$C_{10}$-aryl group or benzyl and n is an integer from 2 to 50, which comprises carrying out the polymerization in the presence of a catalyst, the transition metal component of which is a compound of the formula I

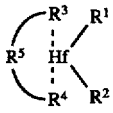

(I)

in which $R^1$ and $R^2$ are identical or different and denote a hydrogen atom, a halogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group.

$R^3$ and $R^4$ are different and denote a mono- or polynuclear hydrocarbon radical, which can form a sandwich structure with the hafnium.

$R^5$ is

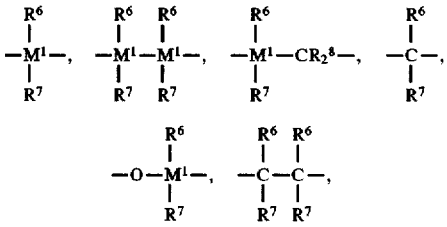

$=BR^6$, $=AlR^6$, —Ge—, —Sn—, —O—, —S—, =SO, $=SO_2$, $=NR^6$, =CO, $=PR^6$ or $=P(O)R^6$, in which $R^5$, $R^7$ and $R^8$ are identical or different and denote a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–C'-arylalkenyl group or a $C_7$–$C_{40}$-alkylaryl group, or $R^6$ and $R^7$ or $R^6$ and $R^8$, in each case with the atoms joining them, form a ring, and $M^1$ is silicon, germanium or tin.

The catalyst to be used for the process according to the invention consists of an aluminoxane and a metallocene of the formula I

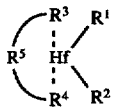

(I)

wherein $R^1$ and $R^2$ are identical or different and denote a hydrogen atom, a $C_1$–$C_{10}$-, preferably $C_1$–$C_3$-alkyl group, a $C_1$–$C_{10}$-, preferably $C_1$–$C_3$-alkoxy group, a $C_6$–$C_{10}$-, preferably $C_6$–$C_8$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$- preferably $C_7$–$C_{10}$-arylalkyl group, a $C_7$–$C_{40}$-, preferably $C_7$–$C_{12}$-alkylaryl group, a $C_8$–$C_{40}$, preferably $C_8$–$C_{12}$-arylalkenyl group or a halogen atom, preferably chlorine.

$R^3$ and $R^4$are different and denote a mono- or polynuclear hydrocarbon radical, which can form a sandwich structure with the hafnium. $R^3$ and $R^4$ are preferably fluorenyl and cyclopentadienyl, it also being possible for the fluorenyl or cyclopentadienyl base structures additionally to carry substituents.

$R^5$ is a single- or multi-membered bridge which links the radicals $R^3$ and $R^4$ and denotes

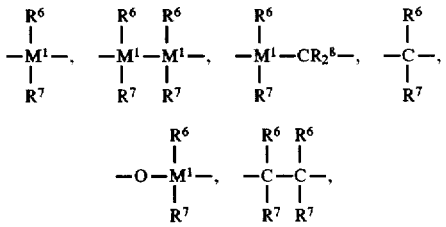

$=BR^6$, $=AlR^6$, —Ge—, —Sn—, —O—, —S—, =SO, $=SO_2$, $=NR^6$, =CO, $=PR^6$or $=P(O)R^6$, in which $R^6$, $R^7$and $R^8$ are identical or different and denote a hydrogen atom, a halogen atom, preferably chlorine, a $C_1$–$C_{10}$-, preferably $C_1$–$C_3$-alkyl group, in particular a methyl group, a $C_1$–$C_{10}$-fluoroalkyl group, preferably a $CF_3$ group, a $C_6$–$C_{10}$-fluoroaryl group, preferably a pentafluorophenyl group, a $C_6$–$C_{10}$-, preferably $C_6$–$C_8$-aryl group, a $C_1$–$C_{10}$-, preferably $C_1$–$C_4$-alkoxy group, in particular a methoxy group, a $C_2$–$C_{10}$-, preferably $C_2C_4$-alkenyl group, a $C_7$–$C_{40}$-, preferably $C_7$–$C_{10}$-arylalkyl group, a $C_8$–$C_{40}$-, preferably $C_8$–$C_{12}$-arylalkenyl group or a $C_7$–$C_{40}$-, preferably $C_7$–$C_{12}$-alkylaryl group, or $R^6$ and $R^7$ or $R^6$ and $R^8$, in each case together with the atoms joining them, form a ring.

$M^1$ is silicon, germanium or tin, preferably silicon or germanium.

$R^5$ is preferably $=CR^6R^7$, $=SiR^6R^7$, $=GeR^6R^7$, —O—, —S—, =SO, $=PR^6$ or $=P(O)R^6$.

The metallocenes described above can be prepared in accordance with the following general equation.

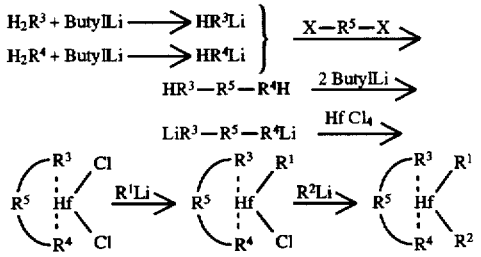

(X = Cl, Br, J, O-Tosyl)

or

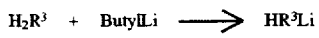

-continued

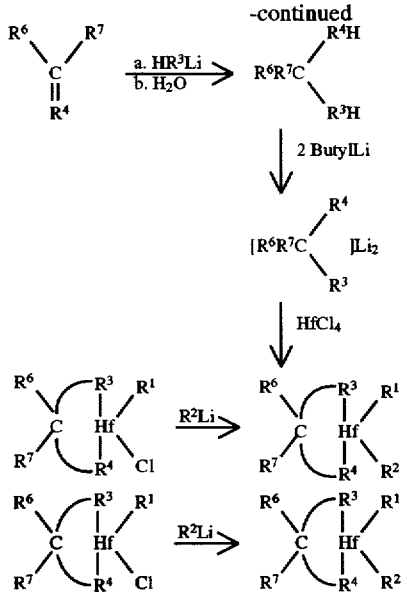

Metallocenes which are preferably employed are (arylalkylidene) (fluorenyl) (cyclopentadienyl)-hafnium diochloride and (diarylmethylene) (fluorenyl) (cyclopentadienyl)-hafnium dichloride. (Methyl(phenyl) methylene) (fluorenyl) (cyclopentadienyl)-hafnium dichloride and (diphenylmethylene) (fluorenyl) (cyclopentadienyl) -hafnium dichloride are particularly preferred here.

The cocatalyst is an aluminoxane of the formula II

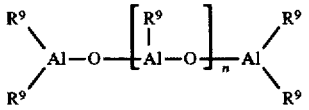

(II)

for the linear type and/or of the formula III

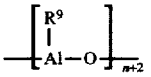

(III)

for the cyclic type. In these formulae, the radicals $R^9$ denote a $C_1$–$C_6$-alkyl group, preferably methyl, ethyl, isobutyl, butyl or neopentyl, or a $C_6$–$C_{10}$-aryl group, preferably phenyl or benzyl. Methyl is particularly preferred. n is an integer from 2 to 50, preferably 5 to 40. However, the exact structure of the aluminoxane is not known.

The aluminoxane can be prepared in various ways.

One possibility is careful addition of water to a dilute solution of an aluminum trialkyl by introducing in each case small portions of the solution of the aluminum trialkyl, preferably aluminum trimethyl, and the water into an initially introduced relatively large amount of an inert solvent and waiting for the evolution of gas to end between each addition.

In another process, finely powdered copper sulfate pentahydrate is suspended in toluene in a glass flask, and aluminum trialkyl is added under an inert gas at about −20° C. in an amount such that about 1 mole of $Cu\text{-}SO_4.5H_2O$ is available for every 4 Al atoms. After slow hydrolysis, alkane being split off, the reaction mixture is left at room temperature for 24 to 48 hours, during which it must be cooled, if appropriate, so that the temperature does not rise above 30° C. The aluminoxane dissolved in the toluene is then filtered off from the copper sulfate and the solution is concentrated in vacuo. It is assumed that in this preparation process the low molecular weight aluminoxanes undergo condensation to higher oligomers, aluminum trialkyl being split off.

Aluminoxanes are furthermore obtained by a procedure in which aluminum trialkyl, preferably aluminum trimethyl, dissolved in an inert aliphatic or aromatic solvent, preferably heptane or toluene, is reacted with aluminum salts containing water of crystallization, preferably aluminum sulfate, at a temperature of −20° to 100° C. The volume ratio here between solvent and the aluminum alkyl used is 1:1 to 50:1—preferably 5:1—and the reaction time, which can be controlled by the splitting off of the alkane, is 1 to 200 hours—preferably 10 to 40 hours.

Of the aluminum salts containing water of crystallization, those which have a high content of water of crystallization are used in particular. Aluminum sulfate hydrate is particularly preferred, above all the compounds $Al_2(SO_4)_3.16H_2O$ and $Al_2(SO_4)_3.18H_2O$, with the particularly high water of crystallization content of 16 and 18 moles of $H_2O$/mole of $Al_2(SO_4)_3$ respectively.

Another variant for the preparation of aluminoxanes comprises dissolving aluminum trialkyl, preferably aluminum trimethyl, in heptane or toluene in the suspending agent which has been initially introduced into the polymerization vessel, preferably in the liquid monomer, and then reacting the aluminum compound with water.

In addition to the processes described above for the preparation of aluminoxanes, there are others which can be used. Regardless of the nature of the preparation, all the aluminoxane solutions have the common feature of a varying content of unreacted aluminum trialkyl which is in free form or as an adduct. This content has an influence on the catalytic activity which has not yet been clarified precisely and differs according to the metallocene compound employed.

It is possible for the metallocene to be preactivated before use in the polymerization reaction with an aluminoxane of the formula (II) and/or (III). The polymerization activity is in this way increased significantly and the grain morphology is improved.

The preactivation of the transition metal compound is carried out in solution. Preferably, in this procedure, the metallocene is dissolved in a solution of the aluminoxane in an inert hydrocarbon. An aliphatic or aromatic hydrocarbon is suitable as the inert hydrocarbon. Toluene is preferably used.

The concentration of the aluminoxane in the solution is in the range from about 1% by weight up to the saturation limit, preferably 5 to 30% by weight, in each case based on the total solution. The metallocene can be employed in the same concentration, but it is preferably employed in an amount of $10^{-4}$ −1 mole per mole of aluminoxane. The preactivation time is 5 minutes to 60 hours, preferably 5 to 60 minutes. The reaction is carried out at a temperature of −78° to 100° C., preferably 0° to 7020 C.

A significantly longer preactivation is possible, but this usually has neither an activity-increasing nor an activity-reducing effect, although it may be entirely appropriate for storage purposes.

The polymerization is carried out in a known manner in solution, in suspension or in the gas phase, continuously or discontinuously, in one or more stages at a temperature of −60° to 200° C., preferably −30° to 100° C., in particular 0° to 80° C.

The total pressure in the polymerization system is 0.5 to 100 bar. The polymerization in the pressure range of 5 to 60 bar, which is of particular interest industrially, is preferred. Monomers of boiling points higher than the polymerization temperature ire preferably polymerized under normal pressure.

In this reaction, the metallocene compound is used in a concentration, based on the transition metal, of $10^{-3}$ to $10^{-7}$, preferably $10^{-4}$ to $10^{-6}$mol of transition metal per $dm^3$ of solvent or per $dm^3$ of reactor volume. The aluminoxane is used in a concentration of $10^{-5}$ to $10^{-1}$ mol, preferably $10^{-5}$ to $10^{-2}$ mol per $dm^3$ of solvent or per $dm^3$ of reactor volume. In principle, however, higher concentrations are also possible.

If the polymerization is carried out as suspension or solution polymerization, an inert solvent which is customary for the Ziegler low pressure process is used. For example, the polymerization is carried out in an aliphatic or cycloaliphatic hydrocarbon; examples of these which may be mentioned are butane, pentane, hexane, heptane, isooctane, cyclohexane and methylcyclohexane.

A benzene or hydrogenated diesel oil fraction can furthermore be used. Toluene can also be used. The polymerization is preferably carried out in the liquid monomer.

Olefins of the formula $R^aCH{=}CHR^b$, in which $R^a$ and $R^b$ are identical or different and denote a hydrogen atom or an alkyl radical having 1 to 28 carbon atoms, it also being possible for $R^a$ and $R^b$ to be bonded as a ring, are polymerized or copolymerized. Examples of such olefins are ethylene, propylene, 1-butene, 1-hexene, 4methyl-1-pentene, 1-octene, norbornene or norbornadiene. Propylene, 1-butene and 4methyl-1-pentene are preferred.

The molecular weight of the polymer can be regulated in a known manner. For example, the molecular weight can be regulated with excess trialkylaluminum, preferably trimethylaluminum present in the aluminoxane solution. Hydrogen is preferably used.

The polymerization can be of any desired duration, since the catalyst system to be used according to the invention exhibits only a slight time-dependent decrease in polymerization activity.

If the polymerization time is relatively long, the high molecular weight content in the polymer increases significantly. A longer residence time in the polymerization system is therefore advisable in order to achieve high average molecular weights. In order to achieve high molecular weights, it is advantageous to maintain a high polymerization temperature, since, in contrast to known processes as the polymerization temperature increases in the polymerization system to be used according to the invention, a higher molecular weight has also simultaneously been found. Furthermore, a higher metallocene activity is also simultaneously achieved at a higher polymerization temperature. This means that lower residual ash contents are obtained in the polymer.

The molecular weight distribution is broad to bimodal at a higher polymerization temperature, and is narrow and monomodal at a lower temperature.

The polymers prepared according to the invention moreover generally exhibit a very high syndiotactic index of more than 90%; in this, the process according to the invention is significantly superior to the known processes.

The following examples are intended to illustrate the invention. In these examples VN=viscosity number in $cm^3/g$ $M_w$=weight-average molecular weight in g/mol $M_n$=number-average molecular weight in g/mol $M_w/M_n$=molecular weight distribution The molecular weight was determined by gel permeation chromatography.

SI=syndiotactic index, determined by $^{13}C$—NMR spectroscopy $s_{pay}$=average syndiotactic block length All the following working operations of metallocene synthesis were carried out under an inert gas atmosphere using absolute solvents.

EXAMPLE 1

(Phenyl(methyl)methylene)(9-fluorenyl)(cyclopentadienyl)-halfniun dichloride

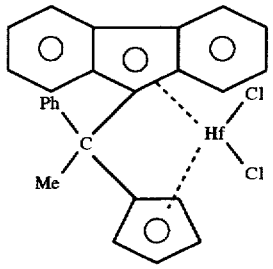

A solution of 61.8 mmol of lithium-fluorene in 50 $cm^3$ of tetrahydrofuran was added to a solution of 11.4 g (67.8 mmol) of 6methyl-6phenylfulvene in 40 $cm^3$ of tetrahydrofuran at room temperature. After the mixture had been stirred at room temperature for 2 hours, 60 $cm^3$ of water were added. The substance which precipitated out was filtered off with suction, washed with diethyl ether and dried under an oil pump vacuum. 19.2 g (84.2%) of 1-cyclopentadienyl-1-(9-fluoroenyl)-ethyl-benzene were obtained (correct elemental analyses; 1 H-NMR spectrum). 10.0 g (19.9 mmol) of the compound were dissolved in 60 $cm^3$ of tetrahydrofuran and 26 $cm^3$ (65 mmol) of a 2.5 molar hexane solution of n-butyllithium were added at 0° C. After the mixture had been stirred for 15 minutes, the solvent was stripped off in vacuo. The dark red residue which remained was washed several times with hexane and dried under an oil pump vacuum. 15.6 g of the red dilithium salt were obtained as the tetrahydrofuran adduct which contained about 30% or tetrahydrofuran. A suspension of 4.78 g (14.9 mmol) of $HfCl_4$ in 70 $cm^3$ of $CH_2CH_2$ was reacted with 14.9 mmol of the dilithium salt and the reaction product was worked up. Crystallization at −35° C. gave 2.6 g (30%) of the hafnocene dichloride compound as orange crystals. Correct elemental analysis.

1 H-NMR spectrum (100 MHz, $CDCl_3$): 7.17–8.20 (m, 11 H, Flu-H,Ph-H), 6.87 (m, 1, Ph-H), 6.12–6.42 (m,3, Ph-H, CpH), 5.82, 5.67 (2xdd,2x1,Cp-H), 2.52 (s,3,$CH_3$).

EXAMPLE 2

Diphenylmethylene(9-fluorenyl)(cyclopentadienyl) hafnium dichloride

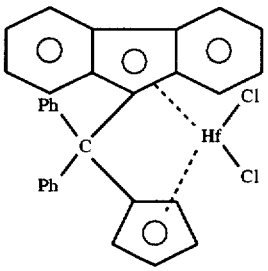

12.3 $cm^3$ (30.7 mmol) of a 2.5 molar hexane solution of n-butyllithium were slowly added to a solution of 5.10 g (30.7 mmol) of fluorene in 60 $cm^3$ of tetrahydrofuran at room temperature. After 40 minutes, 7.07 g (30.7 mmol) of diphenylfulvene were added to the orange solution and the mixture was stirred overnight. 60 $cm^3$ of water were added to the dark red solution, whereupon the solution became yellow-colored, and the mixture, was extracted with ether. The ether phase was dried over $MgSO_4$ and concentrated and the residue was left to crystallize at −3520 C. 5.1 g (42%) of 1-cyclopentadienyl-1-(9-fluorenyl)-diphenylmethine were obtained as a beige powder. 1.25 g (3.15 mmol) of 1-cyclopentadienyl-1-(9-fluorenyl)-diphenylmethane were reacted with 6.3 mmol of butyllithium analogously to Example 1. The dilithium salt was reacted with 1.0 g (3.15 mmol) of $HfCl_4$ analogously to Example 1. Filtration of the orange reaction mixture over a G4 frit and extraction of the filtrate with 100 $cm^3$ of toluene give 0.70 g (34%) of the hafnocene dichloride complex as a yellow-orange powder. Correct elemental analysis. The mass spectrum give M+=644.

1 H-NMR spectrum (100 MHz,$CDCl_3$) 6.85–8.25 (m,16, Flu-H,Ph-H), 6.37 (m,2,Ph-H), 6.31 (t,2,Cp-H), 5.75 (t,2, Cp-M).

EXAMPLE 3

A dry 16 $dm^3$ reactor was flushed with nitrogen and filled with 10 $dm^3$ of liquid propylene 30 cm3 of a toluene solution of methylaluminoxane (corresponding to 40 mmol of Al, average degree of oligomerization of the methylaluminoxane n=20) were then added and the mixture was stirred for 15 minutes.

In parallel to this, 53.0 mg (0.082 mmol) of diphenylmethylene(fluorenyl) (cyclopentadienylhafnium dichloride were dissolved in 15 $cm^3$ of a toluene solution of methylaluminoxane (20 mmol of Al). After 15 minutes, the solution was introduced into the reactor and the polymerization temperature was brought to 60° C. Polymerization was carried out for 5 hours. 3.20 kg of polypropylene, corresponding to a metallocene activity of 12.0 kg of polypropylene/g of metallocene x hour, were obtained. VN=1254 $cm^3/g$; $M_w$=2.34.$10^6$, $M_n$=580.000, $M_w/M_n$=4.0, bimodal molecular weight distribution; SI=96.9%, $n_{syn}$= 39.4; melt flow index 230/5≦0.1 dg/minute.

EXAMPLE 4

The procedure was analogous to Example 3, but 64.4 mg (0.10 mmol) of diphenylmethylene(fluorenyl) (cyclopentadienyl)-hafnium dichloride were employed, the polymerization temperature was 50° C. and the polymerization time was 1 hour. 0.34 kg of polypropylene, corresponding to a metallocene activity of 5.3 kg of polypropylene/g of metallocene x hour, was obtained.

VN=978 $cm^3/g$; $M_w=2.01.10^6$, $M_n=0.61.10^6$, $M_w/M_n=3.3$, bimodal molecular weight distribution; SI=97.0%, $n_{syn}=40.0$; melt flow index 230/5≦0.1 dg/minute.

EXAMPLE 5

The process was analogous to Example 3, but 126.4 mg (0.196 mmol) of diphenylmethylene(fluorenyl) (cyclopentadienyl)-hafnium dichloride were employed, the polymerization temperature was 30° C. and the polymerization time was 2 hours. 0.35 kg of polypropylene, corresponding to a metallocene activity of 1.4 kg of polypropylene/g of metallocene x hour, were obtained.

VN=487 $cm^3/g$; $M_w=672.500$, $M_n=196.500$, $M_w/M_n=3.4$, monomodal molecular weight distribution; SI=97.5%, $n_{syn}=48.0$; melt flow index 230/5=0.1 dg/minute.

Examples 3 to 5 show that a high polymerization temperature must be used to achieve a high molecular weight. At the same time, at the higher polymerization temperature the polymerization activity of the metallocene catalyst system is advantageously higher.

EXAMPLE 6

The procedure was analogous to Example 3, but 66.6 mg (0.114 mmol) of (phenyl(methyl)methylene) (fluorenyl) (cyclopentadienyl)-hafnium dichloride were employed. 1.89 kg of polypropylene, corresponding to a metallocene activity of 5.7 kg of polypropylene/g of metallocene x hour, were obtained.

VN=603 $cm^3/g$, $M_w=806.000$, $M_n=175.000$, $M_w/M_n=4.6$, the molecular weight distribution was bimodal; SI=96.4%, $n_{syn}=38.0$; melt flow index 230/5≦0.1 dg/minute.

EXAMPLE 7

The procedure was analogous to Example 3, but 63.9 mg (0.11 mmol) of (phenyl(methyl)methylene) (fluorenyl) (cyclopentadienyl)-hafnium dichloride were employed, the polymerization temperature was 50° C. and the polymerization time was 1 hour. 0.17 kg of polypropylene, corresponding to a metallocene activity of 2.7 kg of polypropylene/g of metallocene x hour, was obtained.

VN=380 $cm^3/g$; $M_w=434.000$, $M_n=116.000$, $M_w/M_n=3.7$, the molecular weight distribution was bimodal; SI=96.1%, $n_{syn}=37.0$; melt flow index 230/5=0.24 dg/minute.

EXAMPLE 8

The procedure was analogous to Example 3, but 110.3 mg (0.19 mmol) of (phenyl(methyl)methylene) (flouroenyl) (cyclopentadienyl)-hafnium dichloride were employed and the polymerization temperature was 4020 C. 0.65 kg of polypropylene, corresponding to a metallocene activity of 1.2 kg of polypropylene/g of metallocene x hour, was obtained.

VN=576 $cm^3/g$; $M_w=837.500$, $M_n=131.500$, $M_wM_n=6.4$; the molecular weight distribution was bimodal; SI=97.1%, $n_{syn}=40.0$, melt flow index 230/5<0.1 dg/minute.

EXAMPLE 9

The procedure was analogous to Example 3, but 151.1 mg (0.26 mmol) of (phenyl(methyl)methylene) (fluorenyl) (cyclopentadienyl)-hafnium dichloride were employed and the polymerization temperature was 30° C. 0.35 kg of polypropylene, corresponding to a metallocene activity of 0.5 kg of polypropylene/g of metalocene x hour, was obtained. VN=251 $cm^3/g$; $M_w=280.500$, $M_n=108.500$, $M_w/M_n=2.6$; the molecular weight distribution was monomodal; SI=97.5%, $n_{syn}=49.4$; melt flow index 230/5=1.1 dg/minute.

The examples show that a high polymerization temperature must be used to achieve the maximum possible molecular weight. At the same time, the activity of the metallocene catalyst is higher at a higher polymerization temperature than at a lower polymerization temperature. Example 8 shows that instead of a high polymerization temperature, a long polymerization time also leads to a high molecular weight.

EXAMPLE 10

A dry 16 $dm^3$ reactor was flushed with nitrogen and filled with 1.6 $Ndm^3$ (corresponding to 0.1 bar) of hydrogen and with 10 $dm^3$ of liquid propylene. 30 $cm^3$ of a toluene solution of methylaluminumoxane (corresponding to 40 mmol of Al, average degree of oligomerization of the methylaluminumoxane n=20) were then added and the mixture was stirred for 15 minutes.

In parallel with this, 55.7 mg (0.087 mmol) of diphenylmethylene(fluorenyl) (cyclopentadienyl)-hafnium dichloride were dissolved in 15 $cm^3$ of a toluene solution of methylaluminoxane (20 mmol of Al).

After 15 minutes, the solution was metered into the reactor and the polymerization temperature was brought to 60° C. Polymerization was cared out for 1 hour. 1.0 kg of polypropylene, corresponding to a metallocene activity of 18.0 kg of polypropylene/g of metallocene x hour, was obtained.

VN=745 $cm^3/g$; SI=97.5; $M_w=978.000$ $M_n=251.500$, $M_w/M_n=3.9$; melt flow index 230/5=<dg/minute.

According to $^{13}C$-NMR, the polymer chains had no unsaturated chain ends.

EXAMPLE 11

The procedure was analogous to Example 10, but 48.7 mg (0.014 mmol) of (phenyl(methyl)methylene) (fluorenyl)-(cyclopentadienyl)-hafnium dichloride were employed. 1.91 kg of polypropylene, corresponding to a metallocene activity of 7.8 kg of polypropylene/g of metallocene x hour, were obtained.

VN=492 $cm^3g$; $M_w=697.500$; $M_n=131.000$; $M_w/M_n=5.3$, the molecular weight distribution was bimodal; SI=97.5%; melt flow index 230/5=0.1 dg/minute.

According to $^{13}C$-NMR, the polymer chains had no unsaturated chain ends.

EXAMPLE 12

The procedure was analogous to Example 10, but 40 $dm^3$ (corresponding to 2.5 bar) of hydrogen and 60.7 mg (0.104 mmol) of (phenyl(methyl)methylene) (fluorenyl( (cyclopentadienyl)-hafnium dichloride were employed. 2.47 kg of polypropylene, corresponding to a metallocene activity of 8.1 kg of polypropylene/g of metallocene x hour, were obtained.

VN=215 $cm^3/g$; $M_w=218.500$; $M_n=75.500$; $M_w/M_n=2.9$; SI=98.0%; melt flow index 230/5=8.1 dg/minute.

According to $^{13}C$-NMR, the polymer chains had no unsaturated chain ends.

Examples 10 to 12 demonstrate the possibility of regulating the molecular weight by means of addition of hydrogen during the polymerization.

We claim:

1. A process for the prepartion of a syndiotactic polyolefin by polymerization or copolymerization of an ethylene, propylene, 1-butene, or 4methyl-1-pentene olefin which comprises carrying out said process at a temperature of −60° C. to 200° C. under a pressure of 0.5 to 100 bar in solution, in suspension or in the gas phase in the presence of a catalyst which comprises a transition metal component and an aluminoxane of the formula II

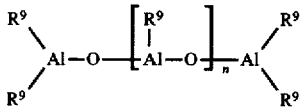

(II)

for the linear type and/or of the formula III

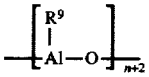

(III)

for the cyclic type, in which, in the formulae II and III, $R^9$ denotes a $C_1$–$C_6$-alkyl group or a $C_6$–$C_{10}$-aryl group or benzyl and n is an integer from 2 to 50, wherein the transition metal component of said catalyst is an (arylalkylidene)(fluoroenyl)(cyclopentadienyl)-hafnium dichloride or a (diarylmethylene)(fluorenyl)(cyclopentadienyl)-hafnium dichloride, in which the aryl of said hafnium compounds is a $C_6$ to $C_{10}$ aryl group and the alkyl of said hafnium compounds is a $C_1$ to $C_{10}$ alkyl group.

2. The process as claimed in claim 1, wherein, the transition metal component comprises (methyl)(phenyl)methylene)(fluorenyl)(cyclopentadienyl)-hafnium dichloride or (diphenylmethylene)-(fluorenyl)(cyclopentadienyl)-hafnium dichloride.

*3. A metallocene compound having the formula*

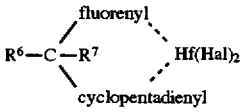

*wherein:*

*Hal is hydrogen,*

*$R^6$ is $C_6$–$C_8$-aryl, and*

*$R^7$ is the same as or different from $R^6$ and is $C_6$–$C_8$-aryl or $C_1$–$C_3$-alkyl.*

*4. A metallocene as claimed in claim 3, wherein Hal is chlorine and $R^6$* is phenyl.

*5. A metallocene as claimed in claim 3, wherein said metallocene is (methyl)(phenyl)-methylene)(fluorenyl)(cyclopentadienyl)-hafnium dichloride.*

*6. A metallocene as claimed in claim 3, wherein said metallocene is (diphenylmethylene)(fluorenyl)(cyclopentadienyl)-hafnium dichloride.*

*7. A catalyst composition comprising a metallocene as claimed in claim 3 and an aluminoxane.*

*8. A catalyst composition comprising a metallocene as claimed in claim 4 and an aluminoxane.*

*9. A catalyst composition comprising a metallocene as claimed in claim 5 and an aluminoxane.*

*10. A catalyst composition comprising a metallocene as claimed in claim 6 and an aluminoxane.*

*11. A catalyst composition as claimed in claim 7, wherein the aluminoxane has the formula II*

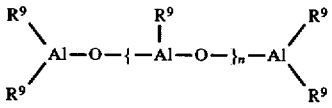

(II)

*for a linear aluminoxane and/or the formula III*

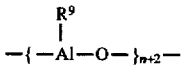

(III)

*for a cyclic aluminoxane, in which, in the formulae II and III,*

*$R^9$ denotes a $C_1$–$C_6$-alkyl group or a $C_6$–$C_{10}$-aryl group or benzyl and n is an integer from 2 to 50.*

*12. A catalyst composition as claimed in claim 11, wherein, in said formula for said metallocene, Hal is chlorine and $R^6$* is phenyl.

* * * * *